United States Patent [19]

Nagy

[11] Patent Number: 4,960,799
[45] Date of Patent: Oct. 2, 1990

[54] STABILIZED AQUEOUS SOLUTIONS OF PHARMACEUTICALLY ACCEPTABLE SALTS OF ORTHO-(2,6-DICHLOROPHENYL)-AMINO-PHENYLACETIC ACID FOR OPTHALMIC USE

[75] Inventor: Ingrid E. Nagy, Berkeley Heights, N.J.

[73] Assignee: Ciba-Geigy Corporation, Ardsley, N.Y.

[21] Appl. No.: 333,772

[22] Filed: Apr. 5, 1989

Related U.S. Application Data

[63] Continuation of Ser. No. 244,547, Sep. 13, 1988, abandoned, which is a continuation of Ser. No. 166,795, Mar. 3, 1988, abandoned, which is a continuation of Ser. No. 945,702, Dec. 23, 1986, abandoned.

[51] Int. Cl.⁵ .......................................... A61K 31/195
[52] U.S. Cl. ................................. 514/567; 514/912; 514/914; 514/970
[58] Field of Search ............... 514/566, 567, 912, 913, 514/914, 915, 970, 840

[56] References Cited

U.S. PATENT DOCUMENTS

| | | | |
|---|---|---|---|
| 3,558,690 | 1/1971 | Sallmann et al. | 260/471 |
| 3,652,762 | 3/1972 | Sallmann et al. | 424/60 |
| 3,932,655 | 1/1976 | Conn | 514/566 |
| 4,087,538 | 5/1978 | Portnoff | 514/914 |
| 4,230,724 | 10/1980 | Cooper et al. | 514/570 |
| 4,234,601 | 11/1980 | Gardocki | 424/319 |
| 4,292,319 | 9/1981 | Tauber et al. | 424/250 |
| 4,309,421 | 1/1982 | Ghyczy et al. | 514/567 |
| 4,349,563 | 9/1982 | Gilbert et al. | 514/914 |
| 4,402,979 | 9/1983 | Shen | 514/914 |
| 4,410,724 | 10/1983 | Takase et al. | 562/456 |
| 4,444,785 | 4/1984 | Mandt et al. | 514/566 |
| 4,474,811 | 10/1984 | Masuda et al. | 424/317 |
| 4,510,128 | 4/1985 | Khanna | 521/32 |
| 4,593,044 | 6/1986 | Metz | 514/557 |
| 4,607,038 | 8/1986 | Ogata et al. | 514/914 |
| 4,614,741 | 9/1986 | Dell et al. | 514/222 |
| 4,647,590 | 3/1987 | Virno | 514/913 |
| 4,652,586 | 3/1987 | Nathanson | 514/913 |
| 4,711,906 | 12/1987 | Stetten et al. | 514/561 |
| 4,826,879 | 5/1989 | Yamamoto et al. | 514/913 |
| 4,829,083 | 5/1989 | Doulakas | 514/970 |
| 4,829,088 | 5/1989 | Doulakas | 514/567 |

FOREIGN PATENT DOCUMENTS

| | | |
|---|---|---|
| 0105635 | 4/1984 | European Pat. Off. . |
| 0142426 | 5/1985 | European Pat. Off. . |
| 58-174309 | 10/1983 | Japan . |
| 58-174310 | 10/1983 | Japan . |
| 1292412 | 10/1972 | United Kingdom . |
| 2093449 | 9/1982 | United Kingdom . |

Primary Examiner—Veronica P. Hoke
Attorney, Agent, or Firm—Irving M. Fishman

[57] ABSTRACT

Storage stable aqueous ophthalmic, substantially isotonic solutions of pharmaceutically acceptable salts of ortho-(2,6-dichlorophenyl) aminophenylacetic acid, and having a pH of about 7.0 to about 7.8, comprising per ml solution:

(a) about 0.1 to about 5.0 mg of a pharmaceutically acceptable salt of ortho-(2,6-dichlorophenyl)aminophenylacetic acid;
(b) about 0.1 to about 10 mg of a pharmaceutically acceptable salt of ethylenediamine tetraacetic acid;
(c) about 0.5 to about 200 mg of a pharmaceutically acceptable solubilizer;
(d) about 0.01 to about 5.0 mg of a pharmaceutically acceptable bacteriostat; and
(e) the remainder water, and the use of such solutions, by topical administration to the eye of a warm blood mammal, for the control or treatment of ocular inflammation.

10 Claims, No Drawings

STABILIZED AQUEOUS SOLUTIONS OF PHARMACEUTICALLY ACCEPTABLE SALTS OF ORTHO-(2,6-DICHLOROPHENYL)-AMINO-PHENYLACETIC ACID FOR OPTHALMIC USE

This application is a continuation of application Ser. No. 244,547, filed Sept. 13, 1988, now abandoned, which is a continuation of Ser. No. 166,795, filed Mar. 3, 1988, now abandoned, which is a continuation of Ser. No. 945,702, filed Dec. 23, 1986, now abandoned.

BACKGROUND OF THE INVENTION

Ortho-(2,6-dichlorophenyl)aminophenylacetic acid and its pharmaceutically acceptable salts are known beta-blocking compounds, useful in the treatment of inflammation. Sodium ortho(2,6-dichlorophenyl)aminophenylacetate, also commonly known as diclofenac sodium, has been shown, for example, in pharmacological studies to possess potent anti-inflammatory and analgesic properties. See, for example, Riess et al., *Scand. J. Rheumatol. Suppl.*, Vol. 22, pp. 17–29 (1978). The use of diclofenac sodium in the form of an aqueous solution in the treatment of ocular inflammation has also been shown. See, for example, M. Agata et al., *Nihon Ganka Gakkai* [Acta Soc. Ophthalmol. Japan], Vol. 87, pp. 19–28 (1983), and M. Agata et al., *Nihon Ganka Gakkai* [Acta Soc. Ophthalmol. Japan], Vol. 88, No. 6, pp. 61–66 (1984).

Aqueous solutions of pharmaceutically acceptable salts of ortho-(2,6-dichlorophenyl)aminophenylacetic acid are useful in the treatment or control of ocular inflammation in mammals, including man, by topical application of an effective amount thereof to the eye, and are particularly advantageous in the control of post-operative inflammation, inter alia, of the type associated with cataract removal, intra-ocular lens replacement or laser tubeculoplasty; for the control of inflammation associated with bacterial conjunctivitis; for the symptomatic relief of vernal conjunctivitis; and for the prevention of miosis in patients undergoing surgery for cataract removal.

Unfortunately, aqueous solutions of ortho-(2,6-dichlorophenyl)aminoacetic acid and salts thereof can slowly decompose into byproducts. Thus, diclofenac sodium aqueous solutions can slowly degrade, for example, upon storage into the corresponding 1-(2,6-dichlorophenyl)-2-indolinone and the like, depending upon the solution temperature and hydrogen ion concentration. See, for example, Larsen et al., *Arch. Pharm. Chemi, Sci. Ed.*, Vol. 8, pp. 100–108 (1980).

In U.S. Pat. No. 4,230,724, ethylenediamine tetraacetic acid is mentioned as a stabilizing chelating agent for 2-(2-fluoro-4-biphenylyl) propionic acid, i.e. florbiprofen, ophthalmic compositions. Also in U.S. Pat. No. 4,474,811, the disodium salt of ethylenediamine tetraacetic acid is recited as a preservative in ophthalmic solutions containing mixtures of 2-(2-fluoro-4-biphenylyl) propionic acid and a cyclodextrin. However, Example 1 of this latter patent illustrates no differences in stability of the compound solutions with and without the disodium salt of ethylenediamine tetraacetic acid in one month storage tests, U.S. Pat. No. 4,474,811 at column 8, lines 32–39.

It is an object of the present invention to provide stable aqueous solutions of pharmaceutically acceptable salts of ortho-(2,6-dichlorophenyl)aminophenylacetic acid containing an effective stabilizing amount of a pharmaceutically acceptable salt of ethylenediamine tetraacetic acid.

It is a further object of the present invention to provide a method of treating or controlling ocular inflammation in a mammal by topical administration of such stabilized aqueous solutions of a pharmaceutically acceptable salt of ortho-(2,6-dichlorophenyl)aminophenylacetic acid.

These and other objects of the present invention will become apparent from the following disclosures.

DETAILED DISCLOSURE OF THE INVENTION

One embodiment of the instant invention relates to a storage stable aqueous substantially isotonic solution of a pharmaceutically acceptable salt of ortho-(2,6-dichlorophenyl)aminophenylacetic acid for topical treatment of ocular inflammation, said solution having a pH of between about 7.0 and about 7.8, comprising, per ml solution:

(a) about 0.1 to about 5.0 mg of a pharmaceutically acceptable salt of ortho-(2,6-dichlorophenyl)aminophenylacetic acid;

(b) about 0.1 to about 10 mg of a pharmaceutically acceptable salt of ethylenediamine tetraacetic acid;

(c) about 0.5 to about 200 mg of a pharmaceutically acceptable solubilizer;

(d) about 0.01 to about 5.0 mg of a pharmaceutically acceptable bacteriostat; and (e) the remainder water.

Suitable pharmaceutically acceptable salts of ortho-(2,6-dichlorophenyl) aminophenylacetic acid and of ethylenediamine tetraacetic acid include those wherein the cation of each is independently selected from the group consisting of the alkali metal, e.g. sodium or potassium, alkaline earth metal, e.g. calcium or magnesium, ammonium, mono-, di-, or tri- loweralkylammonium, e.g. the methylammonium, diethylammonium, or trimethylammonium, hydroxy-substituted mono-, di-, or tri- loweralkylammonium, such as hydroxyethylammonium, di-(hydroxyethyl)ammonium, trihydroxyethyl ammonium or tris(hydroxymethyl)methylasmsonium, cations and the like. Preferred are the alkali metal salts of ortho-(2,6-dichlorophenyl)aminophenylacetic acid, especially the sodium salt, and the alkali metal salts, especially the disodium salt of ethylenediamine tetraacetic acid.

Since the aforementioned salts are present in aqueous solution, the solution can be prepared either by simply adding the respective components including such salts, as such, to the aqueous medium or by forming such salts in situ, for example, by neutralizing the respective acids with a suitable base, or mixture of bases.

Preferably, the amount of the pharmaceutically acceptable salt of ortho-(2,6-dichlorophenyl)aminophenylacetic acid is present in an amount between about 0.1 and about 2.5 mg, more preferably between about 0.5 and about 1.5 mg, per ml total solution.

The pharmaceutically acceptable salt of ethylenediamine tetraacetic acid is preferably present in an amount between about 0.2 to about 5 mg, more preferably between about 0.5 and about 2 mg, per ml total solution.

The amount and type of pharmaceutically acceptable solubilizer, or mixtures thereof, present in component (c) of the present compositions can vary widely. Suitable solubilizers include glycerin, ethanol, tris(hydroxymethyl)aminomethane, propylene glycol, polyvinyl alcohol, polyvinyl pyrrolidone, polyethylene glycol, polyethoxylated $C_6$–$C_{24}$ aliphatic acids, such as polyethoxylated stearic acid esters, polyethoxylated $C_6$–$C_{24}$ aliphatic alcohols, polyethoxylated ethers of $C_6$–$C_{24}$ aliphatic esters of sorbitol anhydrides, such as polyethoxylated sorbitan mono-oleate, polyethoxylated ethers of $C_6$–$C_{24}$ aliphatic esters of glycerin, such as polyethoxylated castor oil, and mixtures thereof.

Preferably, the solubilizer component is present in an amount between about 20 and about 100 mg, more preferably between about 40 and about 80 mg, per ml total solution. Preferred solubilizers include tris(hydroxymethyl)aminomethane and polyethoxylated ethers of castor oil, and mixtures thereof.

Suitable bacteriostats include those commonly employed as ophthalmic preservatives, such as benzalkonium chloride, thimerosal, phenylethyl alcohol, methyl paraben, propyl paraben, chlorhexidine and sorbic acid. Where compatible, mixtures thereof may be employed. Preferred bacteriostats are thimerosal and sorbic acid.

The amount of bacteriostat employed may vary widely, but is preferably present in an amount of between about 0.01 and about 0.1 mg per ml of total solution.

Salts of ethylenediamine tetraacetic acid are known to have been employed with bacteriostats such as thimerosal, e.g., for the purpose of stabilization, as disclosed in U.S. Pat. No. 2,864,884.

However, surprisingly and unexpectedly, it has now been found that the presence of ethylenediamine tetraacetic acid salts exerts a stabilizing effect on the ortho-(2,6-dichlorophenyl)aminophenylacetic acid salt thereby substantially increasing the storage stability of ophthalmic solutions thereof, even under conditions of elevated temperature.

In order to insure that the pH of the ophthalmic solution is maintained between about 7.0 and about 7.8 preferably between about 7.2 and 7.6, the solution is advantageously buffered with a conventional pharmaceutically acceptable buffering agent, such as boric acid, phosphoric acid or a pharmaceutically acceptable salt thereof, such as those salts wherein the cation is as specified above. Preferred salts again include the alkali metal salts, such as the sodium salts. Where the solubilizer component or a constituent thereof, is in the form of a base, such as tris(hydroxymethyl)aminomethane, the buffer may be added in the solution formulation in the form of the free acid to adjust the pH to between about 7.0 and about 7.8, preferably between about 7.2 and about 7.6.

The formulations of the present invention are prepared advantageously by simply mixing the ingredients in the requisite amount of water, optimally with stirring, under ambient or elevated temperatures, e.g. between about 10° and 40° C., until a solution thereof is obtained.

If desired, additional adjuvants, including buffers, antioxidants, tonicity adjusters, thickeners or viscosity modifiers and the like, may be added, e.g. in an amount between about 0.01 mg to about 100 mg, per ml of total solution. Suitable pharmaceutically acceptable adjuvants include mannitol, sorbitol, glucose, hydroxyethylcellulose, sodium chloride, boric acid, sodium tetraborate, sodium phosphate and the like.

The storage stable aqueous solutions of the present invention can be applied to the eye of the mammal for treatment or control of ocular inflammation by topical application, advantageously dropwise, e.g. by use of an eye dropper.

The amount of solution applied to the eye of the mammal in need of the same will generally be between about 0.02 and about 0.2 ml per eye per application, with generally between one and twelve applications per day, depending upon the type and severity of the nature of the ocular inflammation.

The following examples are merely illustrative of the present invention and they should not be considered as limiting the scope of the invention in any way, as these examples and other equivalents thereof will become apparent to those versed in the art in light of the present disclosure.

EXAMPLE 1

To a 4-liter round bottom flask with a nitrogen purge and stirrer there is added 1.6 kg water, U.S.P. While stirring and flushing with nitrogen, the following ingredients are added in order, dissolving each before adding the next:

| | |
|---|---|
| ethoxylated (35 mol) castor oil | 100.0 g |
| boric acid, N.F. | 38.0 g |
| tromethamine, U.S.P. | 12.0 g |
| disodium ethylenediamine tetraacetic acid | 2.0 g |
| thimerosal, U.S.P. | 0.08 g |
| ortho-(2,6-dichlorophenyl)aminophenylacetic acid, sodium salt | 2.00 g |

To the resulting solution there is added water U.S.P., in an amount sufficient to obtain a total solution volume of 2000 ml. The solution is thoroughly mixed and filtered. The pH of the solution is 7.33 and the osmolarity is 313 mmole/kg, containing a 0.1% concentration of the ortho-(2,6-dichlorophenyl)aminophenylacetic acid, sodium salt. The initial concentration of the ortho-(2,6-dichlorophenyl)aminophenylacetic acid sodium salt in solution, as measured by high pressure liquid chromatography, is 0.98 mg/ml. After storage of the formulation for 14 days at 35° C., the formulation contains a concentration of the ortho-(2,6-dichlorophenyl)aminophenylacetic acid sodium salt, as measured by high pressure liquid chromatography of 0.98 mg/ml (average of these runs after storage in 10 ml low density polyethylene ophthalmic dropper and 4 oz. amber glass bottles).

EXAMPLE 2

Analogously to the procedure of Example 1, the following solutions are prepared:

| Ingredient | Quantity per ml | |
|---|---|---|
| Solution A: | | |
| ethoxylated (35 mol) castor oil | 50.0 mg | |
| boric acid | 10.0 mg | |
| sorbic acid N.F. | 2.0 mg | |
| tromethamine U.S.P. | 20.0 mg | |
| ethylenediamine tetraacetic acid | 1.0 mg | |
| mannitol U.S.P. | 23.0 mg | |
| ortho-(2,6-dichlorophenyl)aminophenyl acetic acid, sodium salt | 1.0 mg | |
| purified water U.S.P. qs | 1.0 ml | |
| Solution B: | | |
| ethoxylated (35 mol) castor oil | 50.0 | 50.0 mg |
| boric acid U.S.P. | 15.00 mg | |
| sorbic acid | 2.0 g | |
| tromethamine U.S.P. | 8.0 mg | |
| disodium ethylenediamine tetraacetic acid | 1.0 mg | |
| ortho-(2,6-dichlorophenyl)aminophenyl acetic acid, sodium salt | 1.0 mg | |
| purified water U.S.P. qs | 1 ml | |

Upon storage of solution A and B, both exhibited high stability over extended periods of time.

EXAMPLE 3

To a 12-liter vessel, equipped with a stirrer and nitrogen purge, there is added 9 liters water, U.S.P. While stirring and flushing with nitrogen, the following ingredients are added sequentially to the vessel in order, dissolving each before adding the next:

| | |
|---|---|
| ethoxylated (35 mol) castor oil | 250.0 g |
| sodium phosphate, monobasic | 36.8 g |
| sodium phosphate, dibasic | 109.2 g |
| disodium ethylenediamine tetraacetic acid | 10.0 g |
| thimerosal, U.S.P. | 0.4 g |
| mannitol, U.S.P. | 89.0 g |
| ortho-(2,6-dichlorophenyl)aminophenylacetic acid, sodium salt | 10.0 g |

To the resulting solution there is added water, U.S.P., in an amount sufficient to obtain a total solution volume of 10.0 liters. The solution is thoroughly mixed and filtered. The solution has a pH of 7.15 and osmolarity of 297 mmole/kg.

What is claimed is:

1. A storage stable aqueous substantially isotonic solution of a pharmaceutically acceptable salt of ortho-(2,6-dichlorophenyl)aminophenylacetic acid for the treatment of ocular inflammation, said solution having a pH between about 7.0 and 7.8 and comprising, per ml solution:
   (a) about 0.1 to about 5.0 mg of a pharmaceutically acceptable salt of ortho-(2,6-dichlorophenyl)amino)phenylacetic acid;
   (b) about 0.1 to about 10 mg of a pharmaceutically acceptable salt of ethylenediamine tetraacetic acid;
   (c) about 0.01 to about 5 mg of a pharmaceutically acceptable bacteriostat;
   (d) about 0.5 to about 200 mg of a pharmaceutically acceptable solubilizer, or mixtures thereof; and
   (e) the remainder water.

2. A storage stable aqueous solution according to claim 1, wherein the amount of pharmaceutically acceptable salt of ortho-(2,6-dichlorophenyl)aminophenylacetic acid is between about 0.1 and about 2.5 mg per ml solution.

3. A storage stable aqueous solution according to claim 1, wherein the pharmaceutically acceptable salt of component (a) is the sodium salt.

4. A storage stable aqueous solution according to claim 2, wherein the pharmaceutically acceptable salt of component (a) is the sodium salt.

5. A storage stable aqueous solution according to claim 1, wherein the pharmaceutically acceptable salt of ethylenediamine tetraacetic acid is the disodium salt.

6. A storage stable aqueous solution according to claim 1, wherein component (b) is present in an amount between about 0.2 to about 5 mg per ml solution.

7. A storage stable aqueous solution according to claim 1, wherein the bacteriostat is selected from the group consisting of benzalkonium chloride, thimerosal, phenylethyl alcohol, methyl paraben, propyl paraben, chlorhexidine and sorbic acid.

8. A storage stable aqueous composition according to claim 1, wherein the solubilizer is selected from the group consisting of tris(hydroxymethyl) aminomethane, polyethoxylated ethers of castor oil, and mixtures thereof.

9. A storage stable aqueous composition according to claim 8, wherein the bacteriostat is sorbic acid.

10. A method for the treatment or control of ocular inflammation in a mammal comprising the topical application of an effective amount of a solution according to claim 1, to the eye of said mammal in need of the same.

* * * * *